US010896744B2

(12) United States Patent
Maxson et al.

(10) Patent No.: US 10,896,744 B2
(45) Date of Patent: Jan. 19, 2021

(54) SYSTEMS AND METHODS FOR VALIDATING AND PREDICTING POLYMER FUNCTIONS USING POLYMER PROPERTIES

(71) Applicant: American Chemical Society, Washington, DC (US)

(72) Inventors: Jaron Patrick Maxson, Orem, UT (US); Siang Lee Hong, Canal Winchester, OH (US); Matthew Glenn Dunbar, Canal Winchester, OH (US); Matthew James Toussant, Columbus, OH (US); Yelena Lipskerova, Columbus, OH (US); Dawn Lorraine George, Grove City, OH (US); Yingqi Wu, Columbus, OH (US)

(73) Assignee: American Chemical Society, Washington, DC (US)

( * ) Notice: Subject to any disclaimer, the term of this patent is extended or adjusted under 35 U.S.C. 154(b) by 0 days.

(21) Appl. No.: 16/538,775

(22) Filed: Aug. 12, 2019

(65) Prior Publication Data

US 2020/0051671 A1 Feb. 13, 2020

Related U.S. Application Data

(60) Provisional application No. 62/717,960, filed on Aug. 13, 2018.

(51) Int. Cl.
| | | |
|---|---|---|
| *G01N 33/48* | (2006.01) | |
| *G01N 33/50* | (2006.01) | |
| *G16C 20/70* | (2019.01) | |
| *G16C 20/80* | (2019.01) | |
| *G06N 5/02* | (2006.01) | |

(52) U.S. Cl.
CPC ............... *G16C 20/70* (2019.02); *G06N 5/02* (2013.01); *G16C 20/80* (2019.02)

(58) Field of Classification Search
CPC ........ G16C 20/70; G16C 20/80; G16C 20/40; G06N 5/02; G06N 5/022; G06N 20/00; G06N 5/003
See application file for complete search history.

(56) References Cited

U.S. PATENT DOCUMENTS

| 6,687,621 B2 | 2/2004 | Schneiderman et al. |
| 8,862,438 B2 | 10/2014 | Drabish et al. |
| 2016/0342737 A1 * | 11/2016 | Kaye ..................... G06T 11/206 |

FOREIGN PATENT DOCUMENTS

WO  WO-2015095066 A1 *  6/2015  ............. G16B 40/00

OTHER PUBLICATIONS

Celia Duce et al., Prediction of Polymer Properties from their Structure by Recursive Neural Networks, 27 Macromolecular Rapid Communications, 711-15 (Apr. 18, 2006) DOI: 10.1002/marc. 200600026 (5 pages).

* cited by examiner

*Primary Examiner* — Russell S Negin
(74) *Attorney, Agent, or Firm* — Finnegan, Henderson, Farabow, Garrett & Dunner, L.L.P.

(57) ABSTRACT

In some embodiments, a computer-implemented method for selecting a polymer for an intended use. The method may include: training a selection model based on a graphical dataset, the graphical dataset comprising a node-edge graph identifying relationships between uses and properties of a polymer; receiving, via a user interface, a request comprising the intended use; based on the selection model, determining a polymer for the intended use; and outputting the determined polymer via the user interface.

20 Claims, 7 Drawing Sheets

SYSTEMS AND METHODS FOR VALIDATING AND PREDICTING POLYMER FUNCTIONS USING POLYMER PROPERTIES

CROSS-REFERENCES TO RELATED APPLICATIONS

This application claims priority from U.S. Provisional Patent Application No. 62/717,960, filed Aug. 13, 2018, which is hereby incorporated by reference in its entirety.

FIELD OF THE INVENTION

The present disclosure provides systems and methods for validating and determining polymer functional utility by using polymer identity and associated observed property numeric values deployed in a database and processed by a recursive partitioning algorithm, creating a visual decision tree.

BACKGROUND

Polymer technology targets the creation, characterization, and adaptation of large molecular mass materials for special use in specific applications. Due to their large array of tunable characteristics, polymer materials may be used in a vast array of applications. However, due to the quantity of available polymer materials with differing properties, it is difficult for researches and manufacturers to identify the polymer with optimal properties for their desired application.

No solution exists for predicting or determining a priori what comparative functional utility or capability any of the millions of existing documented polymers. Traditional approaches to predict the uses and properties of a polymer rely on prior knowledge of the polymer or on numerous trials conducted with a number of polymers to identify which is optimal. For example, current chemical databases may list millions of unique polymer structures, making it difficult for a researcher or manufacturer to parse the data to identify a polymer for a desired application without at least some prior knowledge of the desired polymer.

Thus, there exists a need for systems and methods for automatically determining an optimal polymer for a given application or set of desired characteristics.

SUMMARY OF THE INVENTION

For some embodiments of the present invention, a computer-implemented method is provided for selecting a polymer for an intended use. The method may include: training a selection model based on a graphical dataset, the graphical dataset comprising a node-edge graph identifying relationships between uses and properties of a polymer; receiving, via a user interface, a request comprising the intended use; based on the selection model, determining a polymer for the intended use; and outputting the determined polymer via the user interface.

In another embodiment, a computer-implemented method is provided for determining whether a polymer is appropriate for an intended use. The method may include: training a selection model based on a graphical dataset, the graphical dataset comprising a node-edge graph identifying relationships between uses and properties of a polymer; receiving, via a user interface, a request comprising the intended use and the polymer; based on the selection model, determining a likelihood of the polymer being used for the intended use; and outputting the determined likelihood via the user interface.

Aspects of the disclosed embodiments may include tangible computer-readable media that store software instructions that, when executed by one or more processors, are configured for and capable of performing and executing one or more of the methods, operations, and the like consistent with the disclosed embodiments. Also, aspects of the disclosed embodiments may be performed by one or more processors that are configured as special-purpose processor(s) based on software instructions that are programmed with logic and instructions that perform, when executed, one or more operations consistent with the disclosed embodiments.

It is to be understood that both the foregoing general description and the following detailed description are exemplary and explanatory only, and are not restrictive of the disclosed embodiments, as claimed.

BRIEF DESCRIPTION OF THE DRAWINGS

The accompanying drawings, which are incorporated in and constitute a part of this specification, illustrate disclosed embodiments and, together with the description, serve to explain the disclosed embodiments. In the drawings.

DETAILED DESCRIPTION

Figure 1:
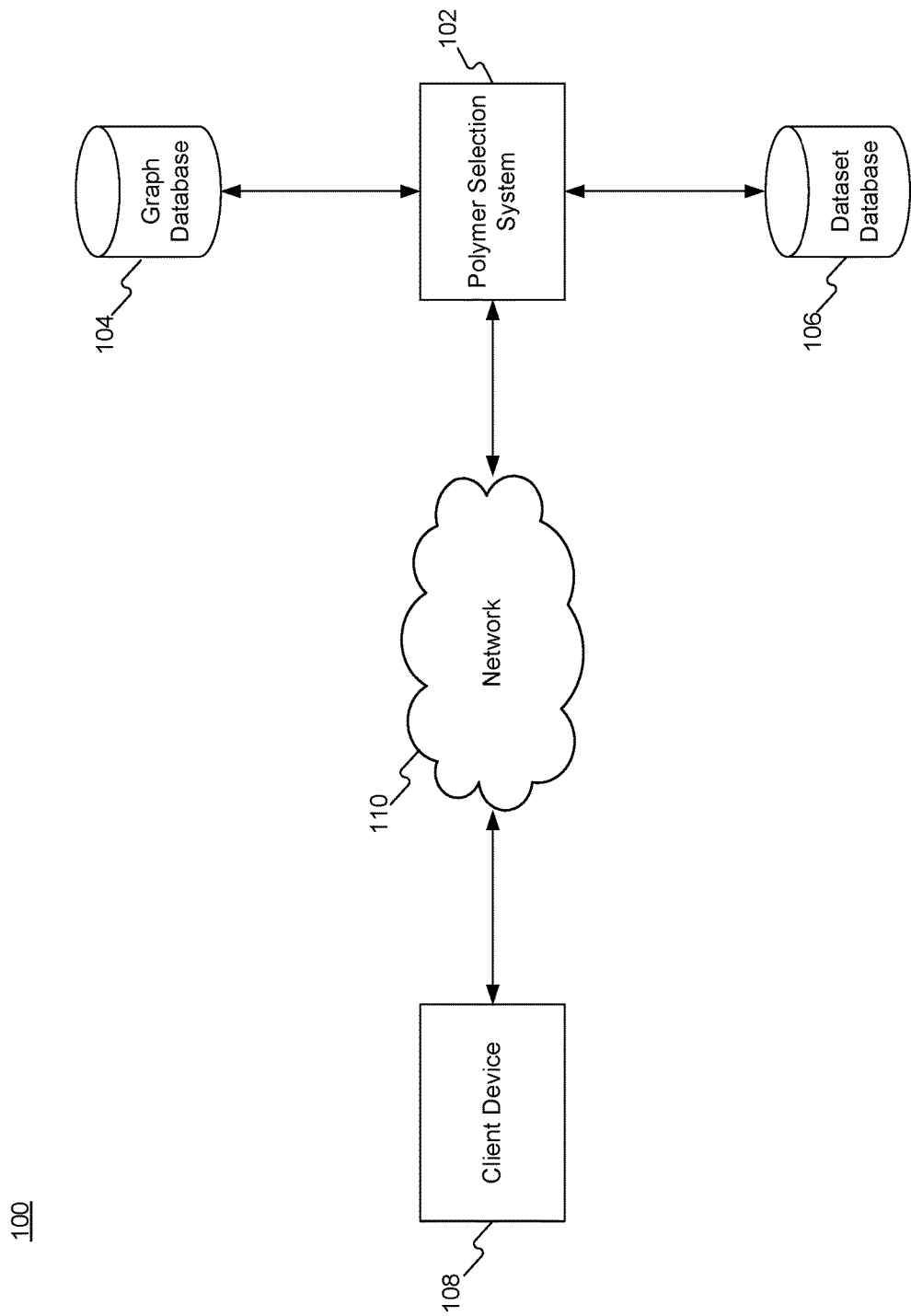
FIG. 1 is a block diagram of an exemplary system for generating optimal polymer predictions, in accordance with disclosed embodiments.

In the following detailed description, numerous specific details are set forth in order to provide a thorough understanding of the disclosed example embodiments. However, it will be understood by those skilled in the art that the principles of the example embodiments may be practiced without every specific detail. Well-known methods, procedures, and components have not been described in detail so as not to obscure the principles of the example embodiments. Unless explicitly stated, the example methods and processes described herein are not constrained to a particular order or sequence, or constrained to a particular system configuration. Additionally, some of the described embodiments or elements thereof can occur or be performed simultaneously, at the same point in time, or concurrently.

Polymer technology targets the creation, characterization, and adaptation of large molecular mass materials for various uses. Current approaches to predict the uses and properties of a polymer rely on prior knowledge of the polymer or on numerous trials conducted with a number of polymers to identify which is optimal for the intended use. However, these current approaches are cumbersome and expensive, and rely on a researcher or manufacturer's prior knowledge of a polymer's existence and properties. Thus, an optimal polymer may exist for an application and remain unknown to the researcher or manufacturer.

Disclosed embodiments provide systems and methods for selecting an optimal polymer for a particular functional use based on a set of one or more desired properties. For example, systems may exploit existing chemical databases and existing literature to train a model for selecting an optimal polymer for a desired application. In some aspects, a molecule's observable and measurable properties, e.g., as solubility, refractive index, melting point, boiling point, dissociation constants, reactivity, toxicity, etc., may affect the functional utility of the polymerized molecule. Thus, based on the properties associated with a particular functional use, the system may select a polymer using a model trained on the documented properties of a set of polymers.

In some aspects, a polymer's functional uses are predicted using recursive partitioning statistical modeling applied to known polymer structures with documented properties. Prediction refinement may be based on an ontology of polymer uses and functional indexing. As used herein, "ontology" refers to a system of cataloging interrelated substances and uses chemical substances. Thus, disclosed embodiments may predict previously unknown or unexpected functional capabilities and uses of polymers based on a predictive model.

To predict functional capabilities of one or more polymers, disclosed embodiments generate a polymer selection model. In some embodiments, a polymer selection system may generate a node-edge graph having polymer identities as nodes and store the node-edge graphs in a graph database. The system may analyze one or more third-party databases to determine polymer properties and their associated values. Third-party databases may also include research databases that are, for example, based on information in peer-reviewed literature. In some embodiments the system may align the polymer properties and their associated values with one or more graphs stored by the graph database to identify polymer entities based on their properties. As used herein, graph data may be aligned such that the data is in an appropriate form for input to a machine learning algorithm. Based on an analysis of the aligned graphs, for example, based on a machine learning algorithm, the system may generate a predictive algorithm configured to predict functional capabilities of a polymer based on its properties. In some embodiments, the system may receive input from a user, via a user interface, indicative of a desired polymer capability or use. For example, the desired capability may be a set of one or more desired parameters, e.g., a certain elasticity, a range of resistivities, a maximum boiling point, etc. In some embodiments, the set of properties associated with the desired use may be determined based on polymer ontology.

Disclosed embodiments may model relationships between functional uses and polymer properties based on one or more third-party databases or datasets. A third-party database may include, for example, a publicly available collection of chemical substances, e.g., CAS Registry, PubChem, ChEMBL, Reaxys, SPRESI, GoStar, and the like. Data available from third-party databases may include a molecule's chemical structure, chemical structure connection information (e.g., the atomic structure, their connections, bond types, hydrogens by valance requirement, charges, etc.), solubility, refractive index, melting point, boiling point, dissociation constants, reactivity, toxicity, glass transition temperature, and the like. In some aspects, third-party databases may be indexed based on a unique identifier associated with each documented molecule.

FIG. 1 depicts exemplary system 100 for selecting an optimal polymer for a given application, consistent with disclosed embodiments. As shown, system 100 may include polymer selection system 102, graph database 104, dataset database 106, and client device 108. Components of system 100 may be connected to each other via network 110.

As will be appreciated by one skilled in the art, the components of system 100 can be arranged in various ways and implemented with any suitable combination of hardware, firmware, and/or software, as applicable. For example, as compared to the depiction in FIG. 1, system 100 may include a larger or smaller number of polymer selection systems, graph databases, dataset databases, client devices and/or networks. In addition, system 100 may further include other components or devices not depicted that perform or assist in the performance of one or more processes, consistent with the disclosed embodiments. The exemplary components and arrangements shown in FIG. 1 are not intended to limit the disclosed embodiments.

Polymer selection system 102 may include a computing device, a computer, a server, a server cluster, a plurality of server clusters, and/or a cloud service, consistent with disclosed embodiments. Polymer selection system 102 may include one or more memory units and one or more processors configured to perform operations consistent with disclosed embodiments. Polymer selection system 102 may include computing systems configured to generate, receive, retrieve, store, and/or provide data models and/or datasets, consistent with disclosed embodiments. Polymer selection system 102 may include computing systems configured to generate and train models, consistent with disclosed embodiments. Polymer selection system 102 may be configured to receive data from, retrieve data from, and/or transmit data to other components of system 100 and/or computing components outside system 100 (e.g., via network 110). Polymer selection system 102 is disclosed in greater detail below (in reference to FIG. 2).

Graph database 104 may be hosted on one or more servers, one or more clusters of servers, or one or more cloud services. Graph database 104 may be connected to network 110 (connection not shown). In some embodiments, graph database 104 may be a component of polymer selection system 102 (not shown).

Graph database 104 may store information in a data structure, e.g., a graph structure. Graph database 104 may be implemented using, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc.

Dataset database 106 may include one or more databases configured to store data for use by system 100, consistent with disclosed embodiments. In some embodiments, dataset database may be configured to store datasets and/or one or more dataset indexes, consistent with disclosed embodiments. Dataset database 106 may include a cloud-based database (e.g., AMAZON WEB SERVICES RELATIONAL DATABASE SERVICE) or an on-premises database. Dataset database 106 may include datasets, model data (e.g., model parameters, training criteria, performance metrics, etc.), and/or other data, consistent with disclosed embodiments. Dataset database 106 may include data received from one or more components of system 100 and/or computing components outside system 100 (e.g., via network 110). In some embodiments, dataset database 106 may be a component of polymer prediction system 102 (not shown).

In some embodiments, dataset database 106 may be a remote, third-party database. Some exemplary third-party chemical databases include CAS Registry, PubChem, ChEMBL, Reaxys, SPRESI, and GoStar. Dataset database 106 may be organized as an array (e.g., a spreadsheet, lab notebook description, database) and/or relational database. Dataset database 106 may store a set of molecules and associated information for each molecule including, but not limited to, boiling point, density, electrical conductivity, electrical resistance, electrical resistivity, glass transition temperature, magnetic moment, median lethal dose, melting point, optical rotatory power, refractive index, tensile strength, etc. In some aspects, dataset database 106 may store ontology information.

Client device 108 may include one or more memory units and one or more processors configured to perform operations consistent with disclosed embodiments. In some embodiments, client device 108 may include hardware, software, and/or firmware modules. Client device 108 may be a user device. Client device 108 may include a mobile device, a tablet, a personal computer, a terminal, a kiosk, a server, a server cluster, a cloud service, a storage device, a specialized device configured to perform methods according to disclosed embodiments, or the like.

At least one of polymer selection system 102, graph storage 104, dataset database 106, or client device 108 may be connected to network 110. Network 110 may be a public network or private network and may include, for example, a wired or wireless network, including, without limitation, a Local Area Network, a Wide Area Network, a Metropolitan Area Network, an IEEE 1002.11 wireless network (e.g., "Wi-Fi"), a network of networks (e.g., the Internet), a land-line telephone network, or the like. Network 110 may be connected to other networks (not depicted in FIG. 1) to connect the various system components to each other and/or to external systems or devices. In some embodiments, network 110 may be a secure network and require a password to access the network.

Figure 2:
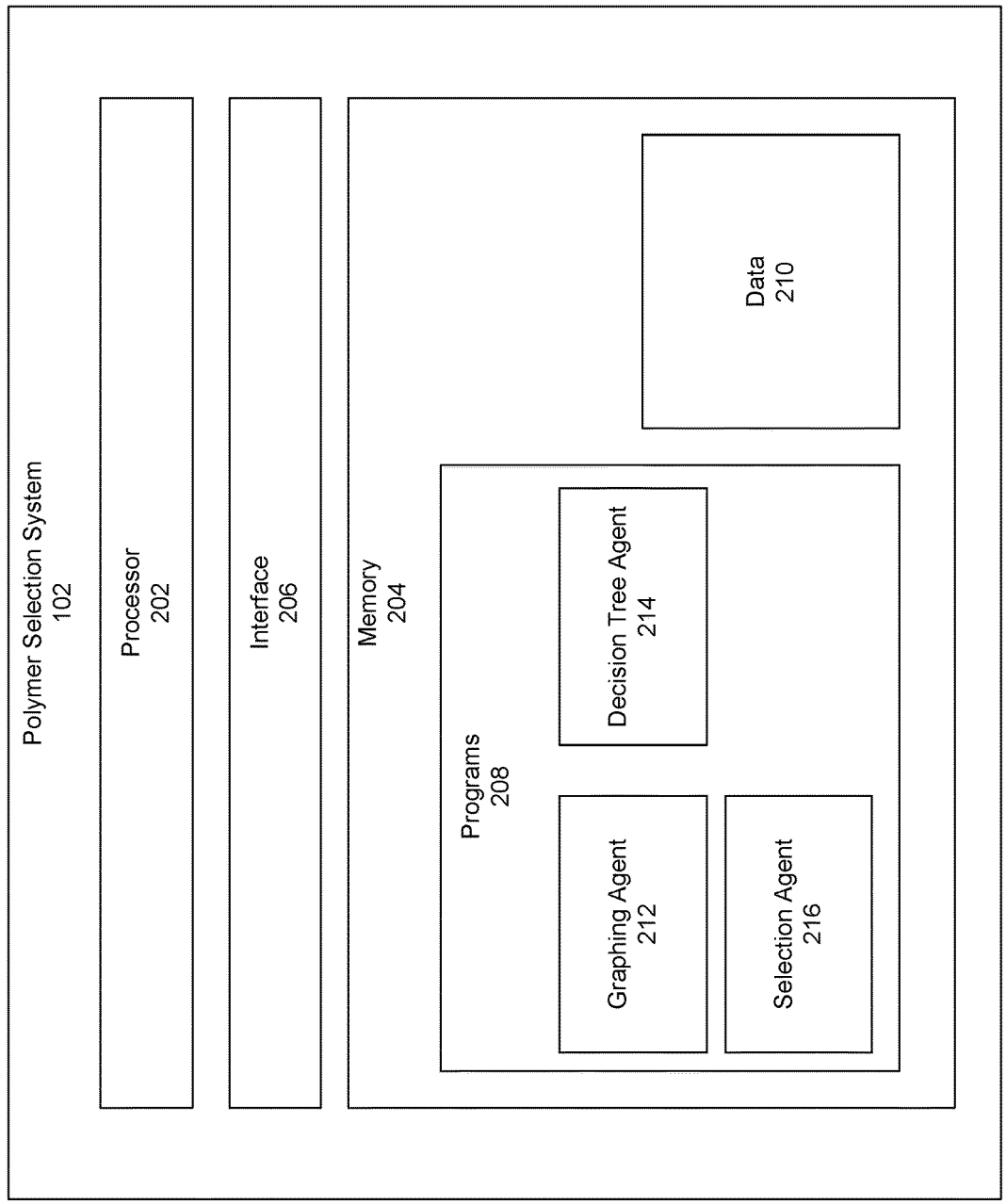
FIG. 2 is a block diagram of an exemplary system for selecting an optimized polymer for a functional use, in accordance with disclosed embodiments.

FIG. 2 depicts an exemplary configuration of polymer selection system 102. As will be appreciated by one skilled in the art, the components and arrangement of components included in polymer selection system 102 may vary. For example, as compared to the depiction in FIG. 2, polymer prediction system 102 may include a larger or smaller number of processors, interfaces or I/O devices, or memory units. In addition, polymer selection system 102 may further include other components or devices not depicted that perform or assist in the performance of one or more processes consistent with the disclosed embodiments. The components and arrangements shown in FIG. 2 are not intended to limit the disclosed embodiments, as the components used to implement the disclosed processes and features may vary.

Processor 202 may comprise known computing processors, including a microprocessor. Processor 202 may constitute a single-core or multiple-core processor that executes parallel processes simultaneously. For example, processor 202 may be a single-core processor configured with virtual processing technologies. In some embodiments, processor 202 may use logical processors to simultaneously execute and control multiple processes. Processor 202 may implement virtual machine technologies, or other known technologies to provide the ability to execute, control, run, manipulate, store, etc., multiple software processes, applications, programs, etc. In another embodiment, processor 202 may include a multiple-core processor arrangement (e.g., dual core, quad core, etc.) configured to provide parallel processing functionalities to allow execution of multiple processes simultaneously. One of ordinary skill in the art would understand that other types of processor arrangements could be implemented that provide for the capabilities disclosed herein. The disclosed embodiments are not limited to any type of processor. Processor 202 may execute various instructions stored in memory 204 to perform various functions of the disclosed embodiments described in greater detail below. Processor 202 may be configured to execute functions written in one or more known programming languages.

Interface 206 may be configured to manage interactions between system 100 and other systems using network 110. In some embodiments, interface 206 may be configured to provide information received from other components of system 100 regarding datasets and/or selection results. In various aspects, interface 206 may be configured to provide data or instructions received from other systems to components of system 100. For example, interface 206 may be configured to receive instructions for generating data models (e.g., type of data model, data model parameters, training data indicators, training parameters, or the like) from another system and provide this information to programs 208. As an additional example, interface 206 may be configured to receive data including experimental data from another system (e.g., in a file, a message in a publication and subscription framework, a network socket, or the like) or from a third-party database and provide that data to programs 208 or store that data in, for example, data 210, graph database 104, and/or dataset database 106.

In some embodiments, interface 206 may include a user interface configured to receive user inputs and provide data to a user (e.g., a data manager or user operating client device 108). For example, interface 206 may include a display, a microphone, a speaker, a keyboard, a mouse, a track pad, a button, a dial, a knob, a printer, a light, an LED, a haptic feedback device, a touchscreen and/or other input or output devices.

Memory 204 may be a volatile or non-volatile, magnetic, semiconductor, optical, removable, non-removable, or other type of storage device or tangible (i.e., non-transitory) computer-readable medium, consistent with disclosed embodiments. As shown, memory 204 may include data 210, including one of at least one of encrypted data or unencrypted data. Consistent with disclosed embodiments, data 210 may include datasets, model data (e.g., model parameters, training criteria, performance metrics, etc.), and/or other data.

Programs 208 may include one or more programs (e.g., modules, code, scripts, or functions) used to perform methods consistent with disclosed embodiments. Programs may include operating systems (not shown) that perform known operating system functions when executed by one or more processors. Disclosed embodiments may operate and function with computer systems running any type of operating system. Programs 208 may be written in one or more programming or scripting languages. One or more of such software sections or modules of memory 204 may be integrated into a computer system, non-transitory computer-readable media, or existing communications software. Programs 208 may also be implemented or replicated as firmware or circuit logic.

Programs 208 may include a graphing agent 212, a decision tree agent 214, a selection agent 216, and/or other components (e.g., agents or modules) not depicted to perform methods of the disclosed embodiments.

Graphing agent 212 may be configured to receive data from dataset database 106 and/or a remote database and generate a node-edge graph having polymer identification nodes where each edge represents a functional use. In some aspects, the node-edge graph of a given polymer may be refined based on ontological relationships and constraints. Thus, the graphs generated by graphing agent 212 may associate each polymer of dataset database 106 with one or more functional uses based on each polymer's documented properties. Polymer properties and functional characteristics may be affected by numerous factors, for instance structure characteristics of the starting monomer or monomers, type of polymerization reaction (typically, addition polymerization or condensation polymerization), conditions of polymerization (e.g., cross-link-forming, molecular size-limiting), post-polymerization modifications. Graphing agent 212 may identify, based on polymer data and ontologies, underlying relationships between properties and functional uses that may not yet be readily documented. For example, a specific set of monomers or catalysts may be used for preparation, which is known to produce certain characteristic products of known use. The presence of the guided preparation may not explicitly be present in the database, e.g., dataset database 106, but may be corrected based on application of the ontology.

In some embodiments, data entities, molecules, and associated information within the dataset may be assembled by any convenient means, including, by using natural language processing programs extracting automatically semantic relations of chemical substances and their uses by populating a template of defined relations and metadata fields, for example, the melting point value for a polymer. This process may then be aligned with design substance-and-property data models. The data model may define the relationships of the data to the model (e.g., the model generated by selection agent 216). For example, defined valid properties are aligned to a substance definition and reference other model specifications. Data deployed by the model may further require effective data harmonization steps of error recognition, data standardization and validation by rule conditions, using technology and human knowledge. This cleaned-up, standardized data according to the model specifications may be first deployed to a preliminary graph database (e.g., Hadoop), further checked for alignment to the data model and data quality standards, and then deployed to a full graph database, e.g., graph database 104, with all nodes and edges relations graphed for substance identities, available properties, functional indexing and uses. These entities so defined and built may represent the means by which a computer implemented method can be employed in a methods for determining whether a polymer is appropriate for an intended use.

Graphing agent 212 may be configured to use one or more machine-assisted assembling modalities to generate a node-edge graph for each identified polymer in dataset database 106. Properties collected and analyzed may include any reported value about a polymer property, including boiling point, density, electrical conductivity, electrical resistance, electrical resistivity, glass transition temperature, magnetic moment, median lethal dose, melting point, optical rotatory power, refractive index, tensile strength, and others.

In some embodiments, a functional capability and application for a polymer are aligned with terminology and relationships of the polymer using functional indexing. For example, data may be normalized such that the data set is consistent. In some embodiments, the alignment is based on the classification of the document where the polymer is described. Categories of classification may include, for example, terms such as surface chemistry, pharmaceuticals, and plastics manufacturing. Document classifications may be stored for example, as tags associated with the document and/or document source. Relationships described in the polymer ontology may include both broad terms and narrow terms in the polymer domain, such as graphite fiber-reinforced plastic, thermosetting, cosmetic microcapsules.

Figure 3:
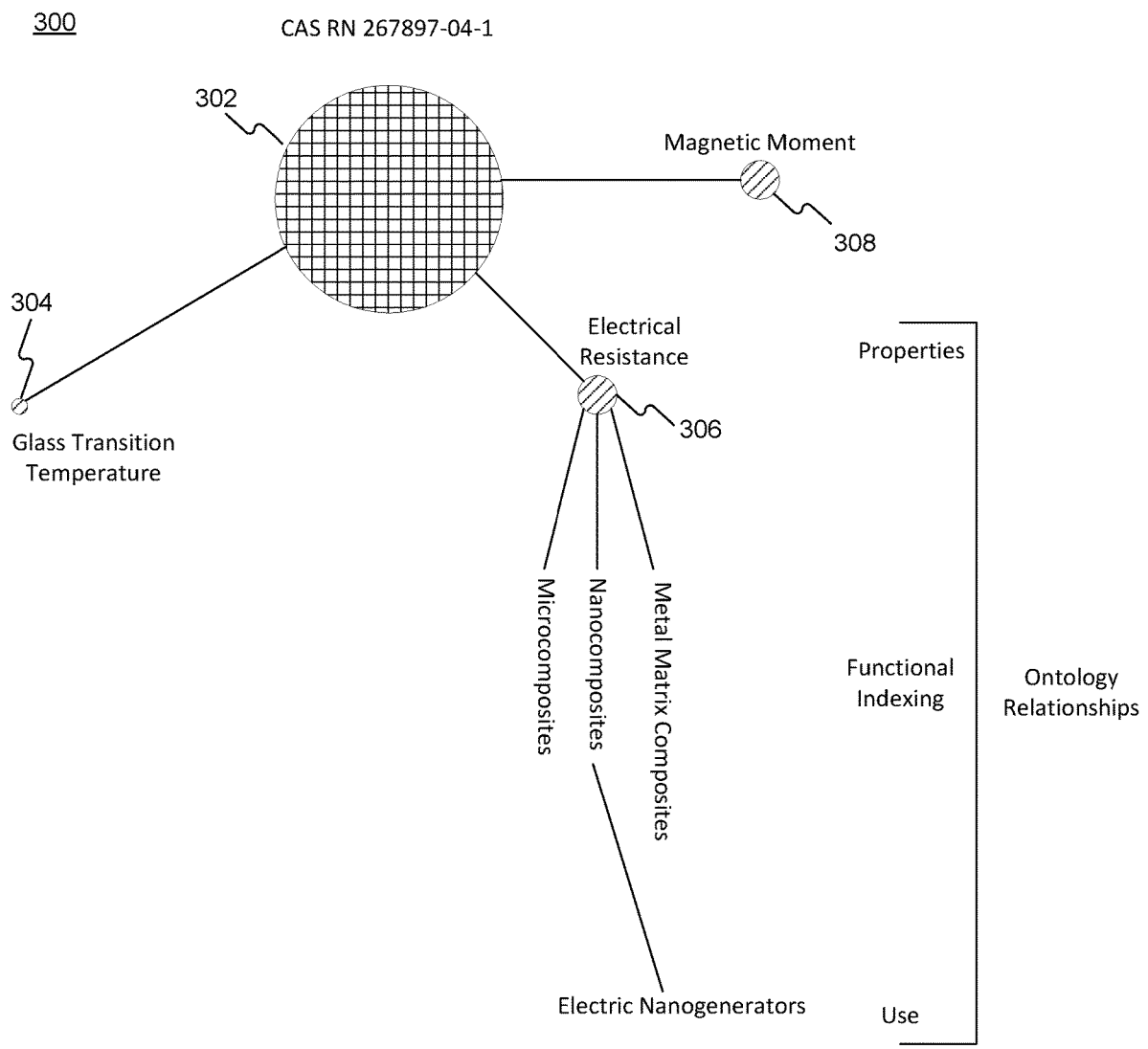
FIG. 3 is an exemplary node-edge graph for a chemical generated by a polymer selection system, in accordance with disclosed embodiments.

FIG. 3 is an exemplary node-edge graph 300 generated by graphing agent 212 and stored in graph database 104. FIG. 3 is an exemplary graph in which the polymer represented by CAS RN 267897-04-1 (Poly[nitrilo(3-methoxy-1,4-phenylene)methylidyne]) is a node 302. In some aspects, each of the relationships (e.g., properties, functional description, and uses) with the chemical substance entity forms a graph edge. For example, the chemical substance's properties (e.g., nodes 304-308), functional description indexing (e.g., thin film, nanocomposite), and designated uses (e.g., flexible piezoelectric nanogenerator) are relationship edges with this chemical substance node 302.

In some embodiments, the placement and size of the nodes may be indicative of the number of entities associated with the node. An entity may be a property measurement, tag, description, use, etc. associated with the polymer.

An exemplary interpretation of the graph depicted in FIG. 3 may be that polymer substance CAS RN 267897-04-1 has an electrical resistance which is suited for use in microcomposites, nanocomposites, and/or metal matrix composites. For example, this use may be indicated in dataset database 106.

Returning to FIG. 2, decision tree agent 214 may be configured to analyze graph data generated by graphing agent 212 and stored in graph database 104 to generate one or more decision trees, each decision tree being associated with a functional capability or use. In some aspects, the decision tree agent 214 may generate the decision tree for each classification using one or more software applications or statistical software environment, e.g., R, SPSS, and the like.

Figure 4:
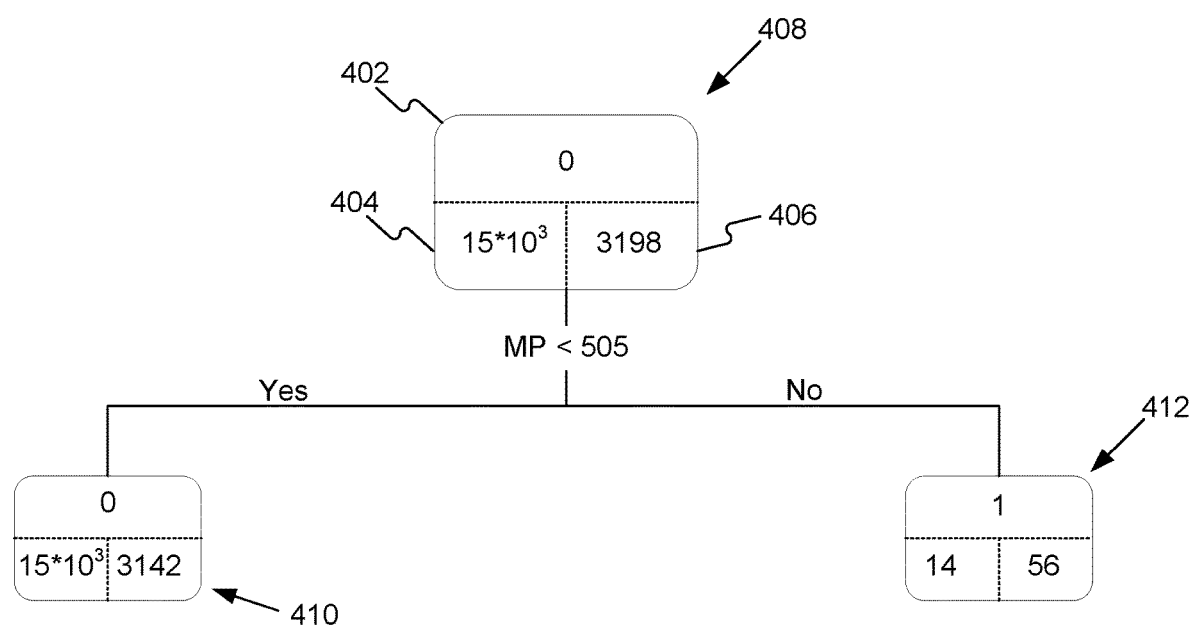
FIG. 4 is an exemplary decision tree generated by a polymer selection system, in accordance with disclosed embodiments.

FIG. 4 is an exemplary decision tree 400 generated by decision tree agent 214. Exemplary decision tree 400 may represent an analysis of polymers' applicability to plastic manufacturing. One or more models generated by selection agent 216, described below, may generate the splitting conditions for each node of the decision tree, for example, based on statistical analysis of one or more graphs of graph database 104.

Node 408 of decision tree 400 may represent a decision, e.g., whether a polymer's melting point is less than 505 K. In more complex examples, e.g., as discussed with references to FIG. 5, each node may represent a number of decisions. Each node (e.g., nodes 408, 410, and 412) of decision tree 400 may indicate three metrics: a binary indicator (402) of whether more than half the sampled population exhibit the behavior in question at the node; the number of polymers at the node exhibiting the behavior in question (404); and the number of polymers at the node not exhibiting the behavior in question (406).

In exemplary decision tree 400, at node 408, of the total population of analyzed polymers, 3198 are associated, based on analysis of graph database 104, with plastic manufacturing applications and 15*103 are not. Of those polymers, at node 410, 3142 polymers are associated with plastic manufacturing, but are unsuitable because their melting point is less than 505 K. Node 412 indicates that, of the polymers analyzed at node 408, 14 polymers are not associated with plastic manufacturing and 56 are associated with, or suitable for use in, plastic manufacturing. Thus, node 412 includes an indicator value of 1, denoting that greater than fifty percent of the polymers evaluated at node 412 are suitable for plastic manufacture and have the desired behavior.

Figure 5:
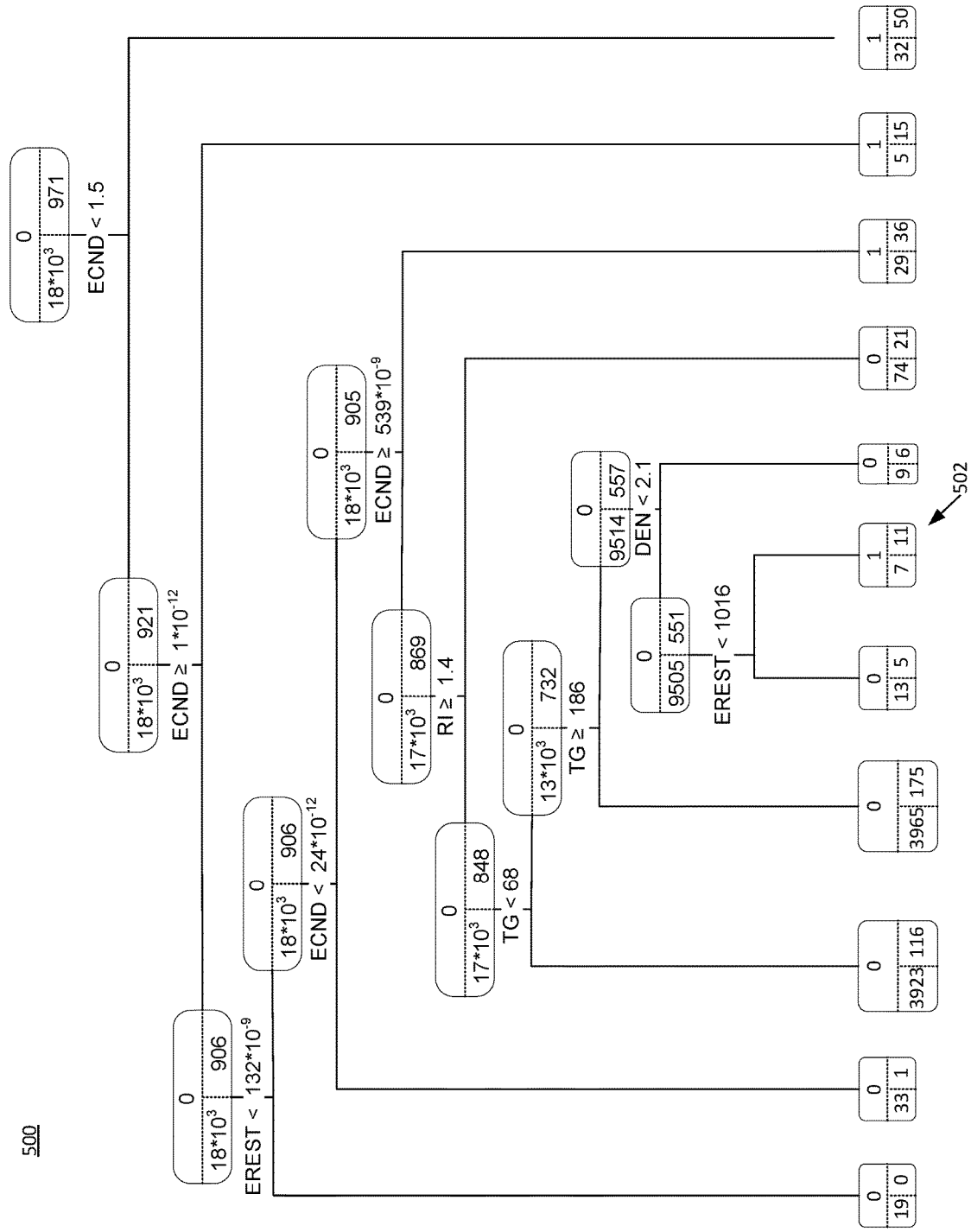
FIG. 5 is another exemplary decision tree generated by a polymer selection system, in accordance with disclosed embodiments.

FIG. 5 is another exemplary decision tree 500 for identifying polymers with desired electrical properties. To reach an endpoint of the decision tree 500, representing the set of polymers that have a set of properties and a desired application, a number of decisions are made, with each decision being determined for the classification of electrical properties based on data stored in graph database 104.

The database, e.g., dataset database 106 and/or graph database 104, may store property and use information. These associations between stored properties and uses may be analyzed statistically to determine patterns. When taken together and optimized, these patterns may be used to generate one or more decision trees.

As an example, node 502 is the result of ten decisions:
1. Electrical conductivity (ECND) is less than 1.5
2. Electrical conductivity (ECND) is greater than or equal to $1.0*10^{-12}$
3. Electrical resistivity (EREST) is greater than $132*10^{-9}$
4. Electrical conductivity (ECND) is greater than $24*10^{-12}$
5. Electrical conductivity (ECND) is greater than $539*10^{-9}$
6. Refractive index (RI) is greater than 1.4
7. Glass transition temperature (TG) is greater than 68
8. Glass transition temperature (TG) is less than 186
9. Density (DEN) is less than 2.1
10. Electrical resistivity (EREST) is greater than 1016

Thus, decision tree 500 may identify 11 polymers out of the analyzed dataset that are suitable for the functional use in an electrical application and having electrical conductivity between $539*10^{-9}$ and 1.5, electrical resistivity greater than 1016, glass transition temperature between 68 and 186, refractive index greater than 1.4, and density less than 2.1. In some embodiments, relationships between properties and functions may not be dependent on the units of measurement of the properties. In other embodiments, graphing agent 212 may clean and normalize data received from dataset database 106 or from other remote databases.

In some embodiments, the decision tree may be further validated or tuned based on ontology data. For example, ontology data may be used to further train the machine learning algorithm used to generate the decision tree. In another embodiment, ontology data may be used to associate identified polymers with other documented uses based on their properties or other entities (e.g., tags, documentation, classifications, etc.) enumerated in the graph database 104.

Returning again to FIG. 2, selection agent 216 may include programs (e.g., scripts, functions, algorithms) to train, implement, store, receive, retrieve, and/or transmit one or more machine-learning models. Machine-learning models may include a neural network model, an attention network model, a generative adversarial model (GAN), a recurrent neural network (RNN) model, a deep learning model (e.g., a long short-term memory (LSTM) model), a random forest model, a convolutional neural network (CNN) model, an RNN-CNN model, an LSTM-CNN model, a temporal-CNN model, a support vector machine (SVM) model, a Density-based spatial clustering of applications with noise (DBSCAN) model, a k-means clustering model, a distribution-based clustering model, a k-medoids model, a natural-language model, and/or another machine-learning model. Models may include an ensemble model (i.e., a model comprised of a plurality of models). In some embodiments, training of a model may terminate when a training criterion is satisfied. Training criterion may include a number of epochs, a training time, a performance metric (e.g., an estimate of accuracy in reproducing test data), or the like. Selection may be configured to adjust model parameters during training. Model parameters may include weights, coefficients, offsets, or the like. Training may be supervised or unsupervised.

In some embodiments, selection agent 216 may be configured to generate models based on instructions received from another component of system 100 and/or a computing component outside system 100 (e.g., via interface 206, from client device 10810, etc.). For example, selection agent 216 may be configured to receive a visual (e.g., graphical) depiction of a machine learning model and parse that graphical depiction into instructions for creating and training a corresponding neural network. Selection agent 216 may be configured to select model training parameters. This selection can be based on model performance feedback received from another component of system 100. Selection agent 216 may be configured to provide trained models and descriptive information concerning the trained models to model storage 104.

Selection agent 216 may be configured to train data models to select, from a dataset, an optimal polymer for a particular functional use, the functional use being provided by a user, e.g., using client device 108. For example, selection agent 216 may be configured to train data models to identify uses of polymers or optimal polymers for a specific use by analyzing graphs of graph database 104 and decision trees generated by decision tree agent 214.

In some embodiments, selection agent 216 may be configured to receive a polymer and a functional use, and output a measure of the polymer's applicability to the identified use. The output of selection agent 216 may be validated based on the known utility of the polymer, e.g., whether the predicted use of the polymer based on the selection model is confirmed in the literature, e.g., in the literature data of dataset database 106. Training the selection algorithm may further include recursively iterating the training process until a desired accuracy is reached. The selection algorithm may further be confirmed or refined using ontology data associated with the desired use and/or specified polymer.

Figure 6:
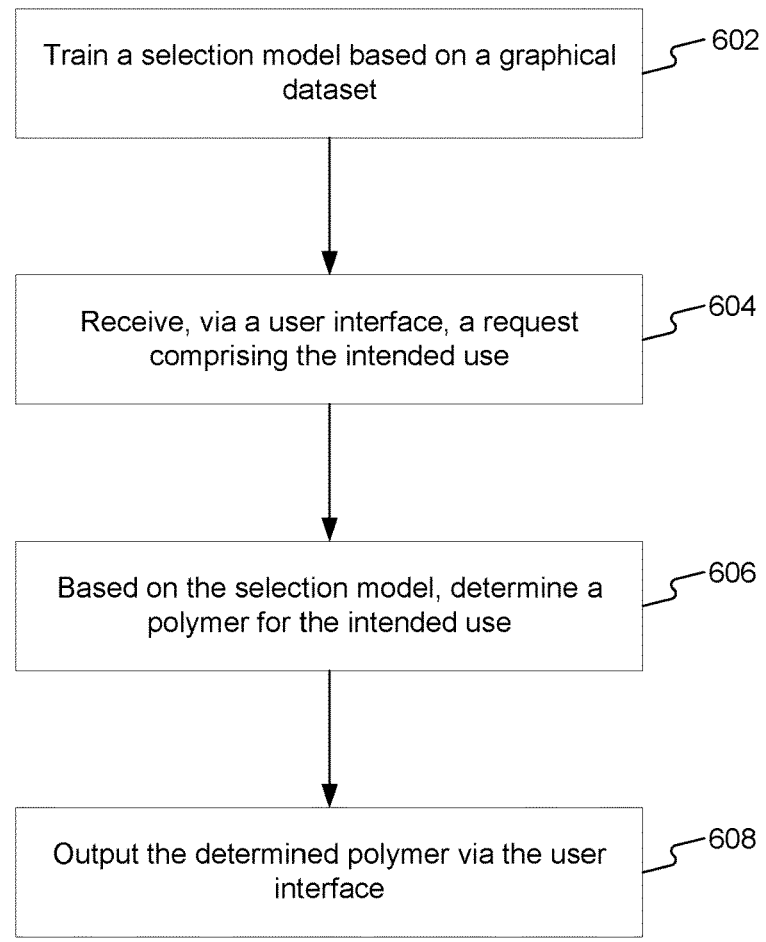
FIG. 6 is a flow diagram of an exemplary method of selecting a polymer for an intended use, in accordance with disclosed embodiments.

FIG. 6 is an exemplary method 600 for selecting a polymer for an intended use, in accordance with disclosed embodiments.

At step 602, the system, e.g., polymer selection system 102, may train a selection model based on a graphical dataset. For example, as described above, graphing agent 212 may receive data from dataset database 106 and generate one or more node-edge graphs based on the received data. The node-edge graphs may be used to provide training data to train the selection model.

At step 604, the system may receive, via a user interface, a request including an intended use. The request may be received from a user operating client device 108. For example, client device 108 may be configured to execute one or more programs or applications enabling client device 108 to communicate with polymer prediction system 108.

At step 606, the system may determine a polymer for the intended use based on the selection model. In some embodiments, the system may determine a list of polymers, for example, based on those polymers identified at a node of a decision tree (e.g., decision tree 500) associated with the intended use or a classification associated with the intended use. In other embodiments, the system may generate a ranked list of polymers based on a measure of fit of each polymer with the intended use.

At step 608, the system may output the determined polymer via the user interface. For example, the system may transmit data indicating the resulting polymer and/or resulting list of polymers to client device 108.

Figure 7:
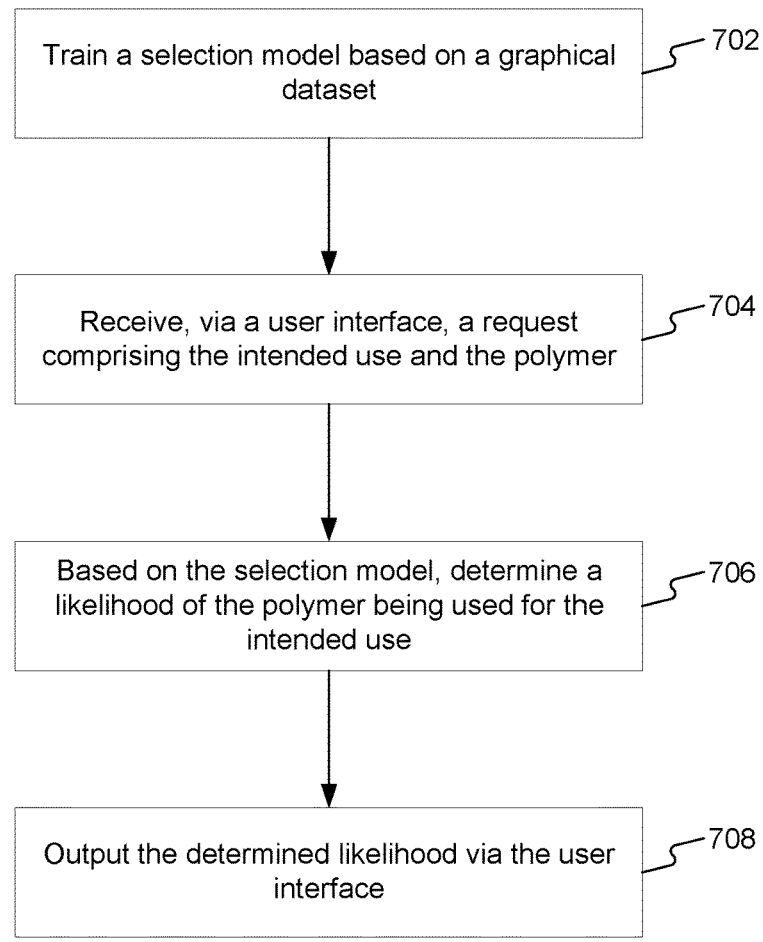
FIG. 7 is a flow diagram of an exemplary method of evaluating a polymer for an intended use, in accordance with disclosed embodiments.

FIG. 7 is an exemplary method 700 for determining whether a polymer is appropriate for an intended use, in accordance with disclosed embodiments.

At step 702, the system, e.g., polymer selection system 102, may train a selection model based on a graphical dataset. For example, as described above, graphing agent 212 may receive data from dataset database 106 and generate one or more node-edge graphs based on the received data. The node-edge graphs may be used to provide training data to train the selection model.

At step 704, the system may receive, via a user interface, a request specifying the intended use and the polymer. For example, a user may wish to determine whether a particular polymer is suited to a particular use or application. The user may provide, via client device 108, for example, an indication of a polymer and an intended use. As previously described, client device 108 may be configured to execute one or more programs or applications enabling client device 108 to communicate with polymer prediction system 108.

At step 706, the system may determine a likelihood of the polymer being used for the intended use. In some embodiments, the system may determine (e.g., via process 600) a set of polymers that are also applicable for the intended use. In some embodiments, the likelihood that a polymer may be appropriate for the intended use may be based on, for example, a measure of fit for the intended use determined by the prediction model. In some embodiments, the system may determine a list of polymers, for example, based on those polymers identified at a node of a decision tree (e.g., decision tree 500) associated with the intended use or a classification associated with the intended use. In other embodiments, the system may generate a ranked list of polymers based on a measure of fit of each polymer with the intended use including the polymer indicated by the user.

At step 708, the system may output the determined likelihood via the user interface. For example, the system may transmit data indicating the resulting likelihood and/or resulting list of polymers to client device 108. In some embodiments, the system may output the likelihood, or a measure of fit, of the requested polymer and may output a list of polymers having a better fit with the intended use.

It is to be understood that the disclosed embodiments are not necessarily limited in their application to the details of construction and the arrangement of the components and/or methods set forth in the following description and/or illustrated in the drawings and/or the examples. The disclosed embodiments are capable of variations, or of being practiced or carried out in various ways.

The disclosed embodiments may be implemented in a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods and computer program products according to various embodiments of the present invention. In this regard, each block in the flowcharts or block diagrams may represent a software program, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A computer implemented method for selecting a polymer for an intended use, the method comprising:
    training a selection model based on a graphical dataset, the graphical dataset comprising a node-edge graph identifying relationships between functional uses and properties of a polymer;
    receiving, via a user interface, a request comprising the intended use of the polymer;
    based on the selection model, determining a polymer for the intended use; and
    outputting the determined polymer via the user interface.

2. The method of claim 1, further comprising:
    generating a decision tree based on the graphical data set; and
    outputting the decision tree via the user interface.

3. The method of claim 2, further comprising:
    based on the decision tree, generate a list of polymers indicated for the intended use; and
    output the list of polymers via the user interface.

4. The method of claim 1, wherein the graphical data set comprises a set of polymers and a set of property measurements associated with each polymer.

5. The method of claim 4, wherein each property of the set of properties is associated with a functional index.

6. The method of claim 1, wherein the intended use is associated with a classification.

7. The method of claim 6, further comprising:
    generating a decision tree based on the classification, the decision tree indicating a set of polymers having properties associated with the intended use.

8. The method of claim 7, further comprising outputting the decision tree via the user interface.

9. A computer implemented method for determining whether a polymer is appropriate for an intended use, the method comprising:
    training a selection model based on a graphical dataset, the graphical dataset comprising a node-edge graph identifying relationships between functional uses and properties of a polymer;
    receiving, via a user interface, a request comprising the intended use of the polymer and the polymer;
    based on the selection model, determining a likelihood of the polymer being used for the intended use; and outputting the determined likelihood via the user interface.

10. The method of claim 9, wherein the intended use is associated with a classification.

11. The method of claim 10, further comprising:
generating a decision tree based on the classification, the decision tree indicating a set of polymers having properties associated with the intended use.

12. The method of claim 11, further comprising outputting the decision tree via the user interface.

13. The method of claim 10, further comprising:
determining, based on the decision tree, an ordered list of polymers based on the likelihood of each polymer being used for the intended use; and
outputting a list of polymers having a greater likelihood than the requested polymer.

14. A system for selecting a polymer for an intended use, the system comprising:
at least one processor; and
a memory storing instructions, that when executed by the at least one processor, cause the processor to:
train a selection model based on a graphical dataset, the graphical dataset comprising a node-edge graph identifying relationships between functional uses of a polymer and properties of a polymer;
receive, via a user interface, a request comprising the intended use;
based on the selection model, determine a polymer for the intended use; and
output the determined polymer via the user interface.

15. The system of claim 14, wherein the instructions further cause the processor to:
generate a query based on the determined polymer, wherein the query is configured to retrieve functional use data from an ontology database; and
validate the determined polymer based on the retrieved functional use data.

16. The system of claim 14, wherein the intended use is associated with a classification.

17. The system of claim 14, wherein the instructions further cause the processor to:
generate a decision tree based on the classification, the decision tree indicating a set of polymers having properties associated with the intended use.

18. The system of claim 14, wherein the instructions further cause the processor to;
determining, based on the decision tree, an ordered list of polymers based on the likelihood of each polymer being used for the intended use; and
outputting a list of polymers.

19. The system of claim 14, wherein each node of the node-edge graph represents an entity.

20. The system of claim 19, wherein an entity comprises at least one of: a chemical, a polymer, a property, a tag, or a definition.

* * * * *